(12) United States Patent
Chen et al.

(10) Patent No.: US 7,842,238 B2
(45) Date of Patent: Nov. 30, 2010

(54) FULLY AUTOMATED MICROARRAY PROCESSING SYSTEM

(75) Inventors: Chia-Chun Chen, Hsinchu (TW);
Jinq-Yu Jiang, Taipei (TW);
Kuo-Hsiung Lin, Miaoli County (TW);
Jie-Len Huang, Hsinchu (TW);
Hung-Ju Su, Hsinchu (TW);
Chun-Hung Huang, Hsinchu County (TW); Shang-Chi Lin, Tainan County (TW)

(73) Assignee: Industrial Technology Research Institute, Hsinchu (TW)

( * ) Notice: Subject to any disclaimer, the term of this patent is extended or adjusted under 35 U.S.C. 154(b) by 499 days.

(21) Appl. No.: 11/929,455

(22) Filed: Oct. 30, 2007

(65) Prior Publication Data

US 2009/0110598 A1 Apr. 30, 2009

(51) Int. Cl.
*G01N 21/00* (2006.01)
(52) U.S. Cl. .............................. 422/65; 422/66; 422/67; 422/99; 422/100; 436/180

(58) Field of Classification Search ............. 422/65–67, 422/99–100; 436/180
See application file for complete search history.

(56) References Cited

U.S. PATENT DOCUMENTS

| 5,192,506 A * | 3/1993 | Kureshy et al. ............... 422/64 |
| 6,238,910 B1 | 5/2001 | Custance et al. |
| 6,790,651 B2 | 9/2004 | Tanaka et al. |
| 2005/0013736 A1* | 1/2005 | McKeever .................. 422/63 |
| 2006/0003440 A1 | 1/2006 | Streit et al. |

* cited by examiner

*Primary Examiner*—Jyoti Nagpaul (57) ABSTRACT

An automated microarray processing system includes a microarray housing assembly module, an incubation module, a washing module and at least one automated transport module. With the automated transport module being mechanically moved among the microarray housing assembly module, the incubation module and the washing module, biochemical reaction of a reaction region of a microarray and a biological sample solution disposed therebetween is automatically performed, and the reacted microarray is automatically cleaned when the biochemical reaction of the microarray is completed.

19 Claims, 7 Drawing Sheets

FULLY AUTOMATED MICROARRAY PROCESSING SYSTEM

BACKGROUND OF THE INVENTION

1. Field of the Invention

The invention relates to an automated microarray processing system, and more particularly to a fully automated microarray processing system to automatically perform biochemical reaction of a microarray and to clean the reacted microarray when the biochemical reaction of the microarray is completed.

2. Description of the Related Art

Conventionally, most of biochemical reaction of a microarray and cleaning process thereof are manually operated. However, the related processes are complicated and time-consuming, thus, costs and working hours cannot be effectively decreased.

U.S. Pat. No. 6,238,910 discloses an apparatus for automatically hybridizing nucleic acid samples. The apparatus includes a carrier for receiving a DNA microarray, a fluid control module, and a temperature control module for precisely controlling fluid contacting and temperature of the DNA microarray. The pipe of the fluid control module is connected to the carrier, and the surface of the DNA microarray is directly cleaned while the DNA microarray is disposed on the carrier. As such, hybridization signals may be distributed, however, by dead zones of the cleaning liquid.

U.S. Patent No. 2006/0003440 discloses a device and process unit for providing a hybridization chamber to hybridize nucleic acid samples, proteins or tissue sections on a slide. Cleaning process of the slide is performed in the device, however, similar to the above, hybridization signals may be distributed due to dead zones of the cleaning liquid.

U.S. Pat. No. 6,790,651 discloses a hybridization reaction apparatus and hybridization method. A reaction solution or a washing solution is injected with a pump and discharged with a pump into and from a case which accommodates a substrate immobilized with biological substances. That is, the flow of the reaction solution or washing solution received in the case must depend on the power of the pump.

BRIEF SUMMARY OF THE INVENTION

The invention provides an automated microarray processing system for automatically performing biochemical reaction of a reaction region of a microarray with biological sample solution disposed therebetween and for automatically cleaning the reacted microarray when the biochemical reaction of the microarray is completed, thereby preventing hybridization signals from being distributed by dead zones of cleaning liquid.

An embodiment of the automated microarray processing system comprises a microarray housing assembly module, an incubation module, a washing module and at least one automated transport module.

The microarray housing assembly module comprises an accommodating room utilized to receive the biological sample solution with at least one bubble therein. The incubation module is utilized to rotatably carry and thermally modulate the microarray housing assembly module. The washing module comprises at least one tank containing cleaning fluid. The automated transport module is utilized to mechanically hold the microarray housing assembly module received with the microarray, the biological sample solution and the bubble to access to the incubation module, and mechanically remove the microarray housing assembly module from the incubation module to access the reacted microarray from the microarray housing assembly module to the tank of the washing module. The removal of the microarray from the microarray housing assembly module and the cleaning process of the removed microarray are completed in the cleaning fluid of the tank of the washing module, and therefore the biological sample solution located on the immersed microarray is washed by the cleaning fluid of the tank of the washing module. Depending on the requirements, the microarray may be proceeding for several cleaning processes by the cleaning fluids of the other tanks.

The automated transport module comprises a mobile robot with at least two degrees of freedom.

The automated microarray processing system further comprises a temperature control module to thermally modulate the biological sample solution. The temperature range of the biological sample solution modulated by the temperature control module is $0°C.\sim100°C$.

The automated microarray processing system further comprises a biological sample feeding module utilized to supply the power for receiving or applying the biological sample solution. The biological sample feeding module further comprises a pipette tip securely fixed and utilized to receive the biological sample solution, thereby applying the biological sample solution on the reaction region of the microarray. The automated microarray processing system further comprises a tip-rack storing module utilized to automatically supply the pipette tip. The tip-rack storing module stores a plurality of tip racks utilized for storing the pipette tips. When the pipette tips of the tip rack are depleted, the used tip rack can be automatically replaced by a new one, i.e., a new tip rack provided with new pipette tips, from the tip-rack storing module.

Generally, the pipette tip is made of plastic for serving as a disposable component. Due to the biological sample feeding module being not directly contacted by the biological sample solution, cross contamination between the samples can be prevented.

The microarray housing assembly module further comprises a first mold plate utilized to receive the biological sample solution, a second mold plate utilized to position the microarray, and a gasket disposed between the first and second mold plates. The microarray housing assembly module can be assembled or disassembled by the automated transport module. More specifically, the accommodating room is formed by the gasket, the first mold plate, and the microarray disposed between the first and second mold plates. The incubation module comprises at least one carrier utilized to fix the microarray housing assembly module and to rotate with respect to a first axis.

In other embodiments, each carrier of the incubation module can be independently rotated about a second axis different from the first axis. The first and second axes are substantially parallel. The first axis is substantially parallel to a horizontal plane.

The automated microarray processing system further comprises a thermal-controlling device utilized to modulate the inner temperature of the microarray housing assembly module. The automated microarray processing system further comprises a drying module utilized to dry the microarray moistened by the cleaning fluid when the microarray is removed from the cleaning fluid of the tank of the washing module.

Additionally, the invention provides a first apparatus configured by the microarray housing assembly module, the incubation module, the temperature control module, the first automated transport module and the second automated transport module, thereby to automatically perform biochemical reaction of the microarray and the biological sample solution. Additionally, the invention provides a second apparatus configured by the incubation module, the washing module, the drying module and the automated transport module, thereby to automatically clean a microarray attached with a biological sample solution disposed thereon.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
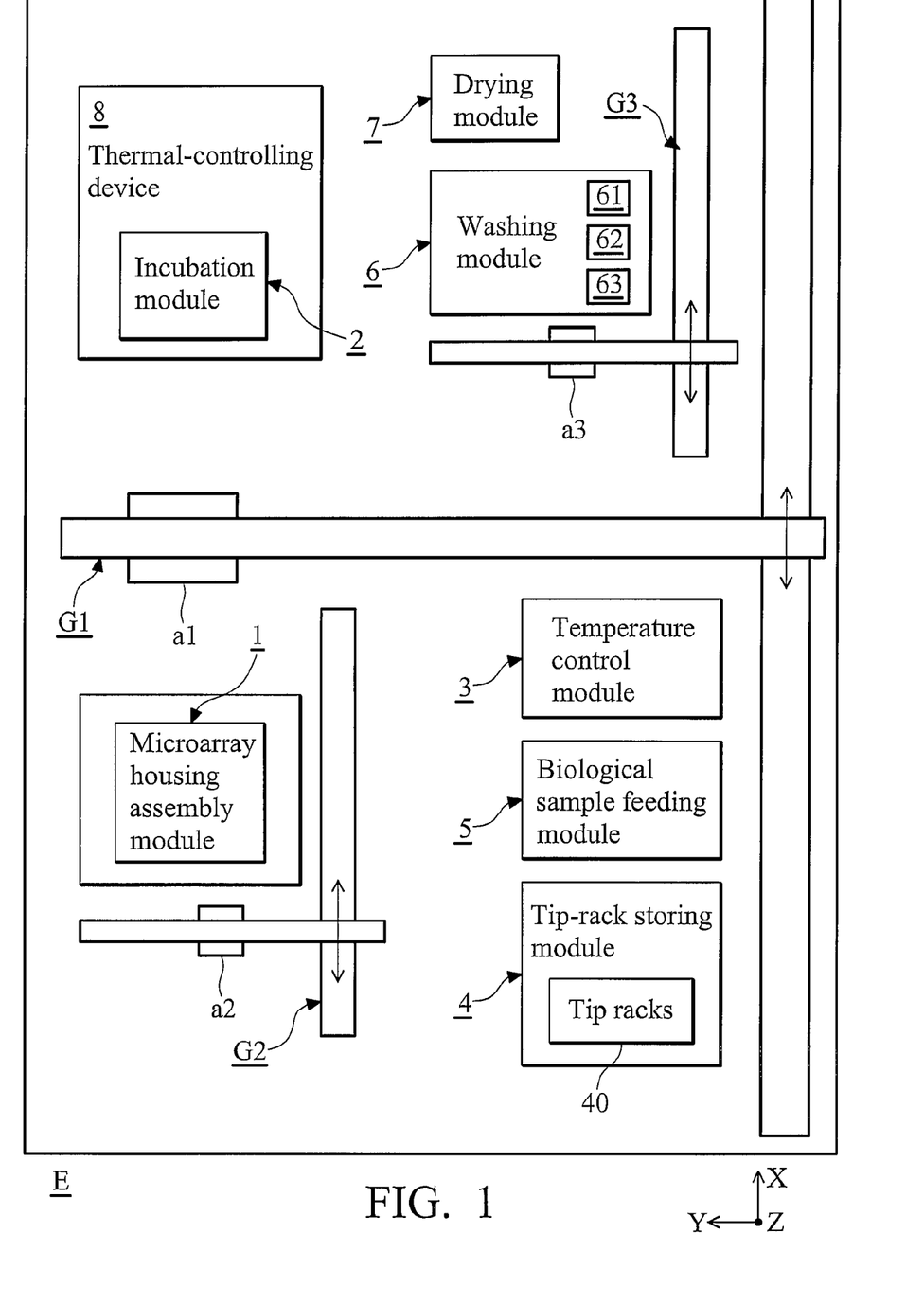
FIG. 1 is a schematic view of a configuration of an automated microarray processing system of the invention.

In FIG. 1, an automated microarray processing system E is automatically configured to perform biochemical reaction of a reaction region of a microarray and a biological sample solution disposed therebetween and to clean the reacted microarray when the biochemical reaction of the microarray is completed.

The automated microarray processing system E comprises a microarray housing assembly module 1, an incubation module 2, a temperature control module 3, a tip rack 40, a tip-rack storing module 4, a biological sample feeding module 5, a washing module 6, a drying module 7, a thermal-controlling device 8, a first automated transport module G1, a second automated transport module G2 and a third automated transport module G3. The incubation module 2 enclosed by the thermal-controlling device 8 is utilized to receive and carry the microarray housing assembly module 1, thereby modulating the inner temperature of the microarray housing assembly module 1 by the thermal-controlling device 8. In the embodiment, the thermal-controlling device 8 is an oven utilized to control the temperature of the incubation module 2. In another embodiment, the thermal-controlling device 8 may dispose on the incubation module 2. The thermal-controlling device 8 is utilized to control the temperature of the incubation module 2 from the room temperature to 80° C.

Basically, the microarray housing assembly module 1, the incubation module 2, the temperature control module 3, the first automated transport module G1 and the second automated transport module G2 are configured as a first apparatus to automatically perform biochemical reaction of a microarray and a biological sample solution. On the other hand, the incubation module 2, the washing module 6, a drying module 7, the first automated transport module G1 and the third automated transport module G3 are configured as a second apparatus to automatically clean a microarray attached with a biological sample solution disposed thereon.

The first, second and third automated transport modules G1, G2 and G3 comprise robots a1, a2 and a3, respectively. Defined by a Cartesian coordinate system X-Y-Z, it is seen that the automated microarray processing system E is mainly set on X-Y plane, and each robot a1, a2 and a3 of the first, second and third automated transport modules G1, G2 and G3 provides at least two degrees of freedom. With the first, second and third automated transport modules G1, G2 and G3 moved among the described components of FIG. 1, all processes of the first and second apparatuses are automatically performed.

Figure 2A:
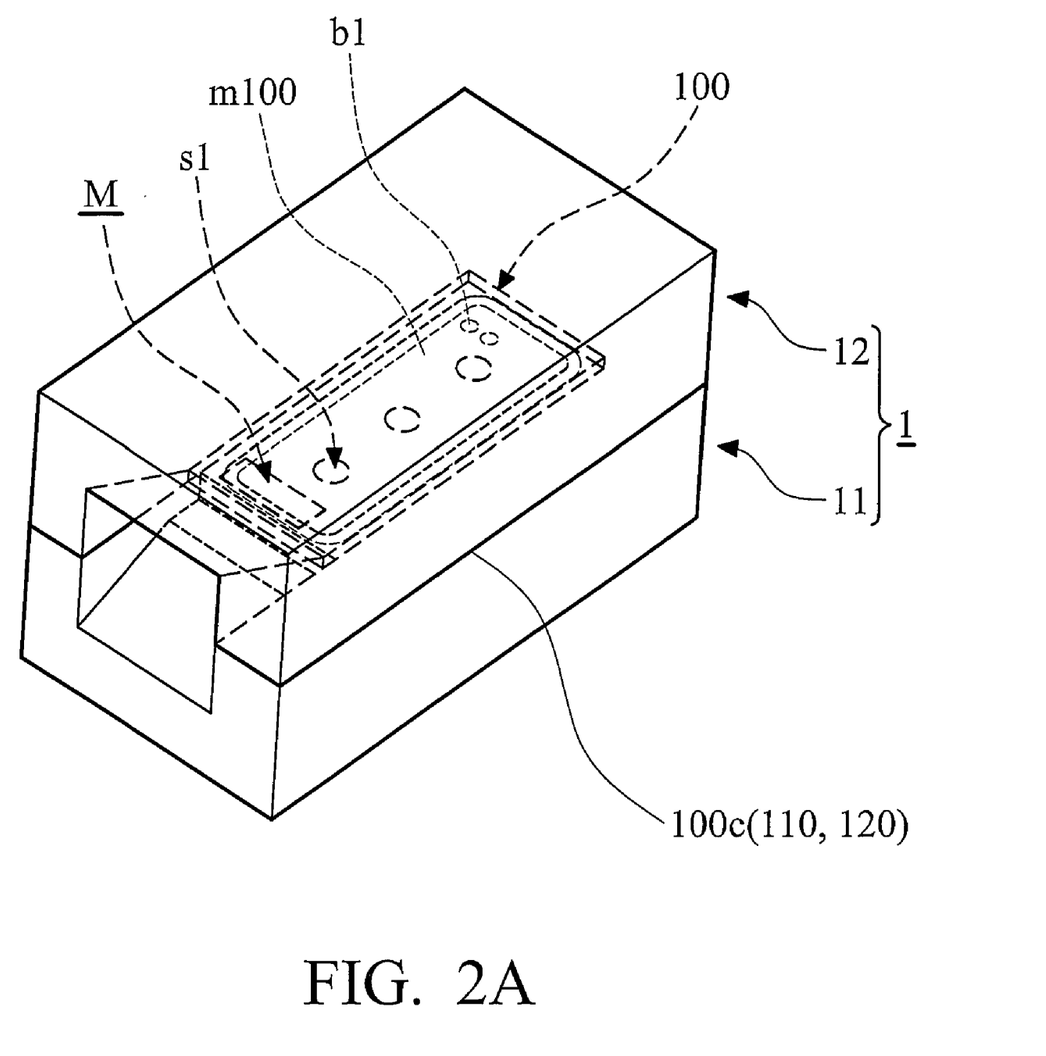
FIG. 2A is a perspective view of a microarray housing assembly module of the invention.
Figure 2B:
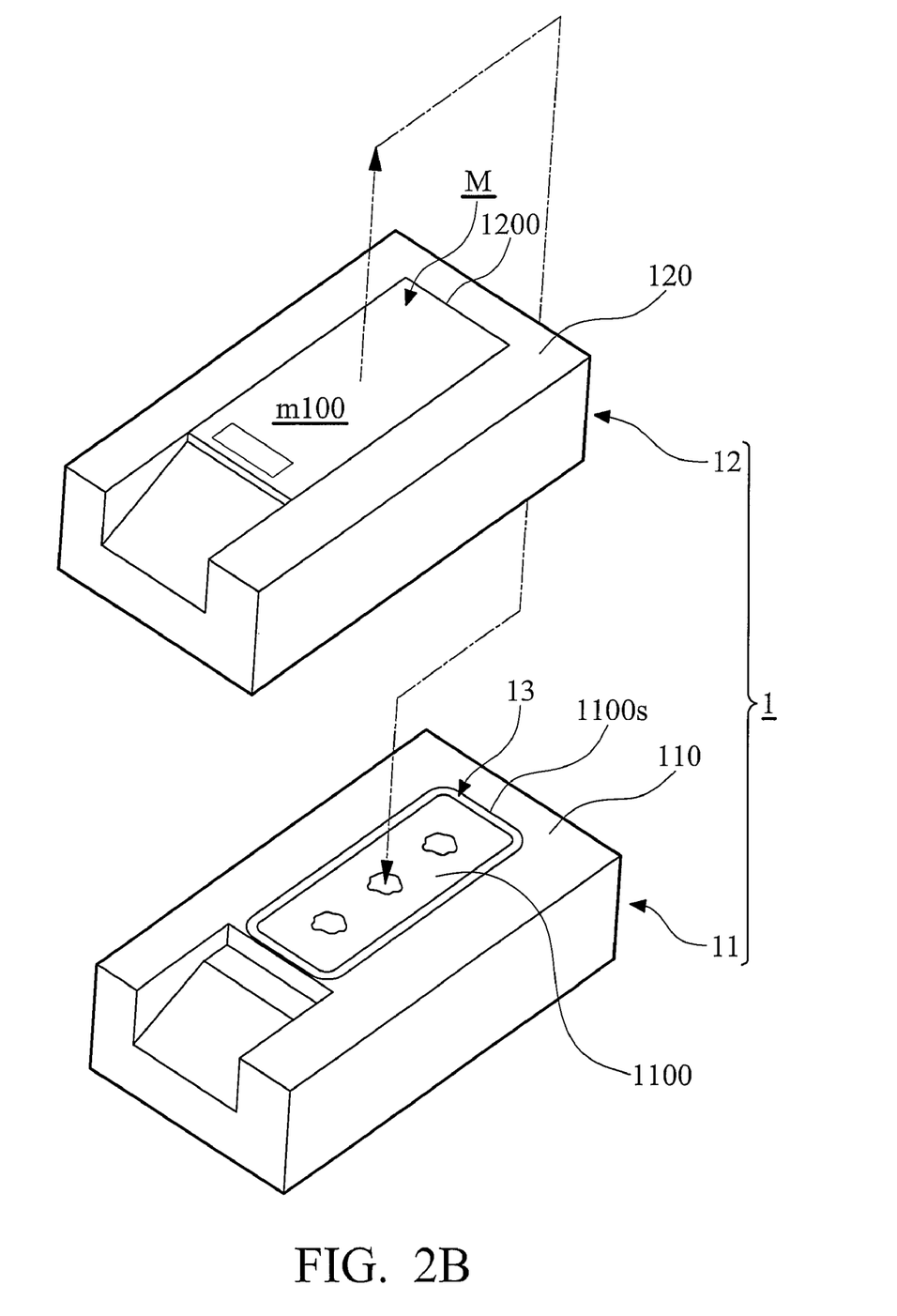
FIG. 2B is an exploded view of the microarray housing assembly module of FIG. 2A.

FIG. 2A is a perspective view of a microarray housing assembly module 1, and FIG. 2B is an exploded view of the microarray housing assembly module 1 of FIG. 2A. The microarray housing assembly module 1 is a holder formed by a first mold plate 11 and a second mold plate 12. The first and second mold plates 11 and 12 are respectively provided with a first conjunctive surface 110 and a second conjunctive surface 120, and a conjunctive area 100c is formed between the first and second mold plates 11 and 12.

Figure 3:
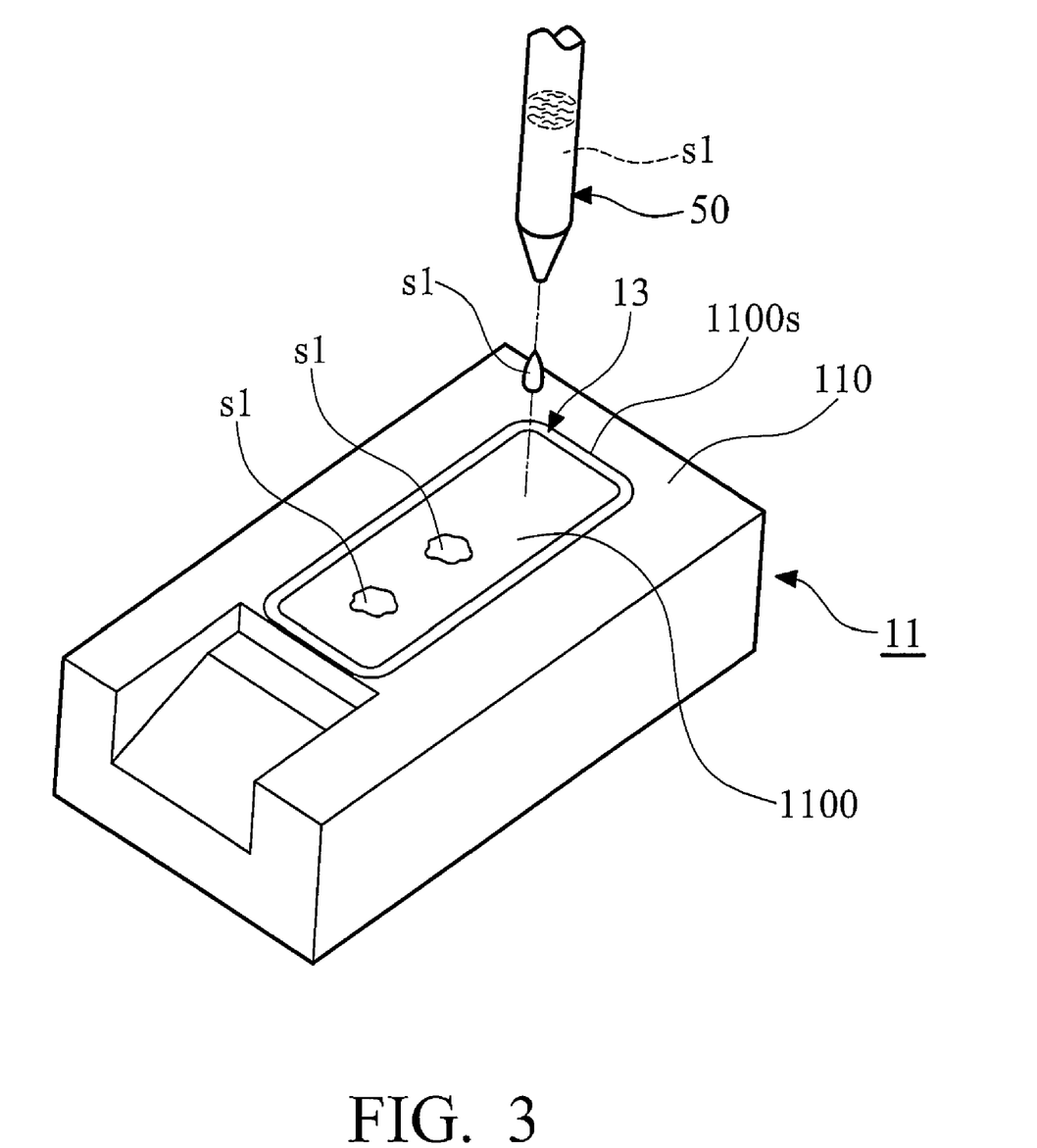
FIG. 3 is a schematic view of a pipette tip applying drops of biological sample solution on a first mold plate of a microarray housing assembly module.
Figure 4A:
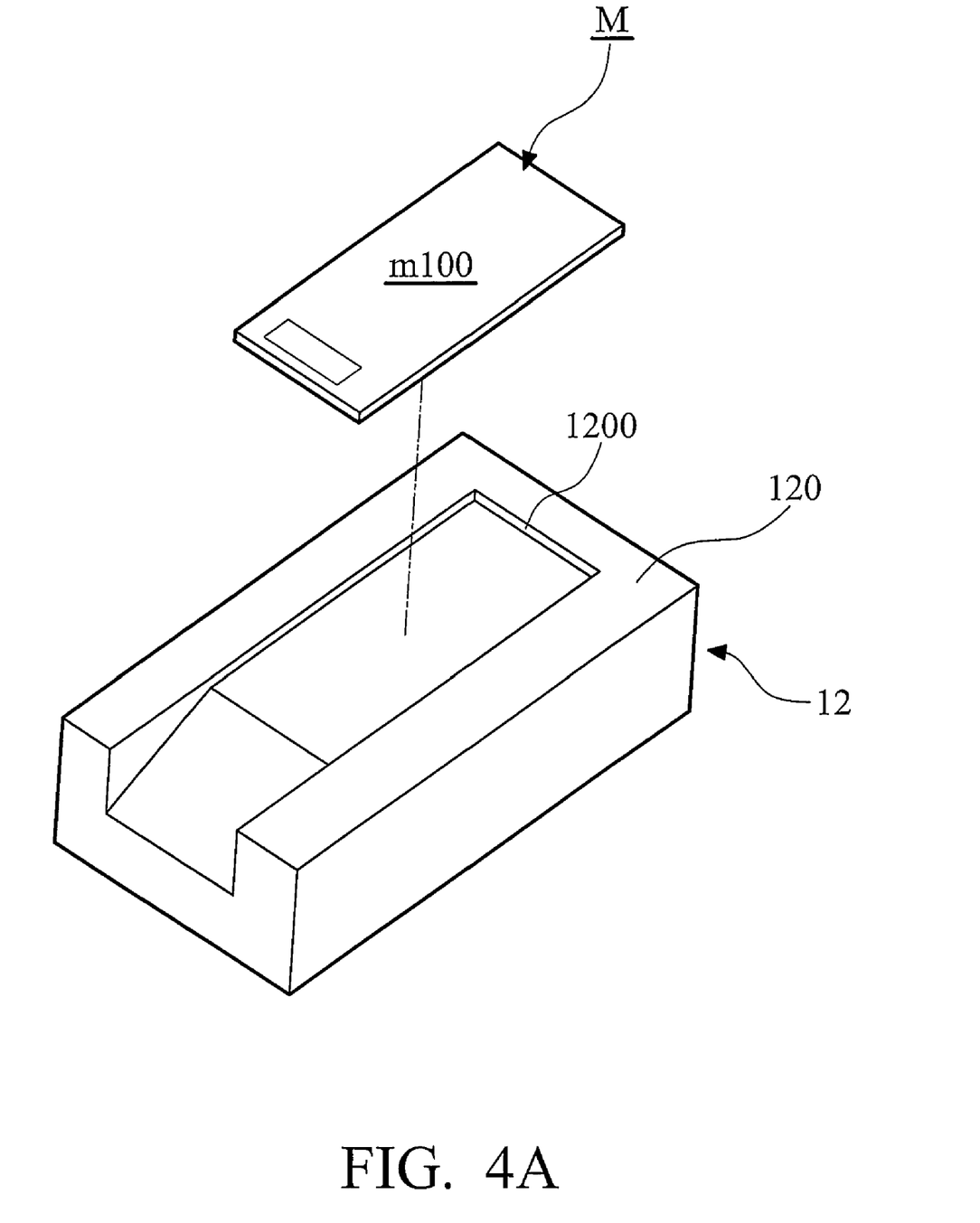
FIG. 4A is a schematic view of a second mold plate of the microarray housing assembly module prior to installation of the microarray thereon.
Figure 4B:
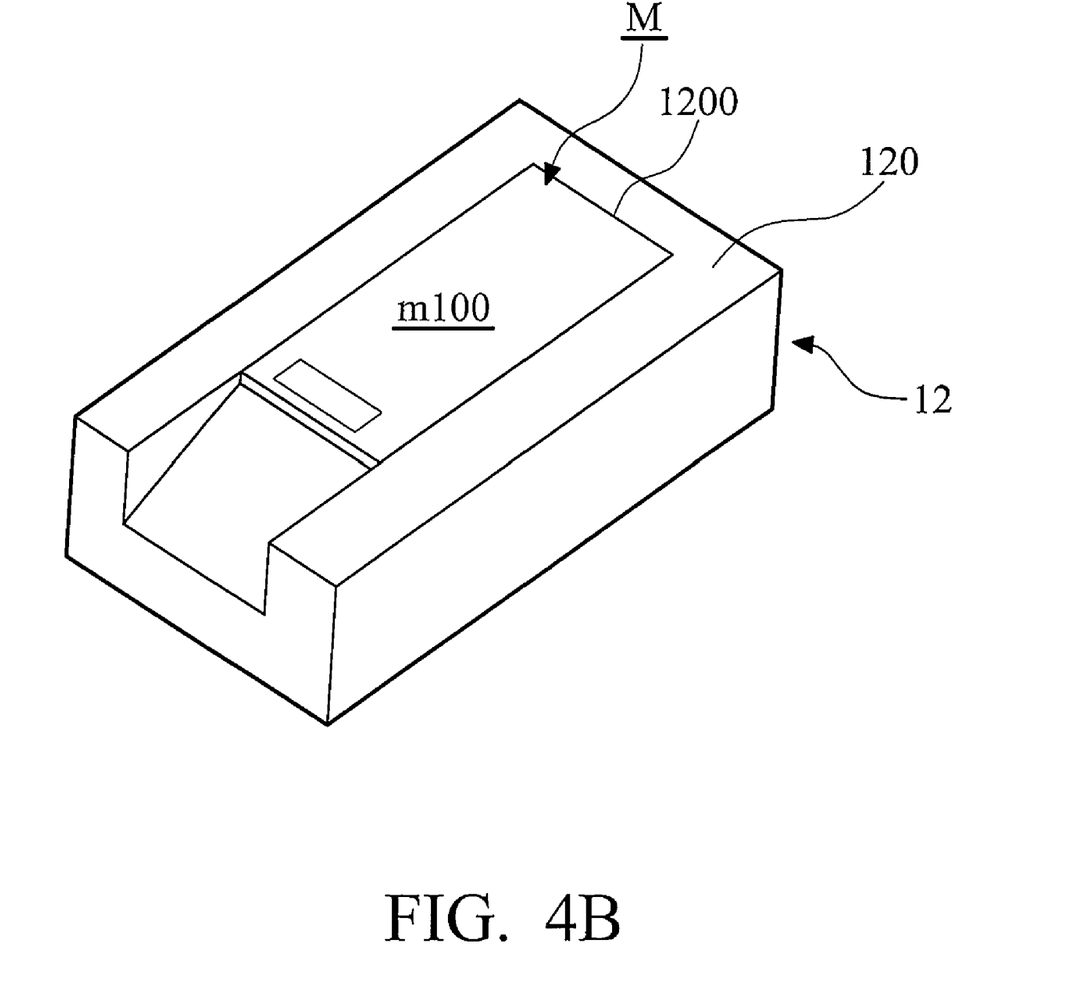
FIG. 4B is a schematic view of the second mold plate of the microarray housing assembly module installed with the microarray thereon.

In FIG. 3, the pipette tip 50 disposed in the biological sample feeding module 5 utilized to receive the biological sample solution s1 and apply three drops of biological sample solution s1 on the first mold plate 11 of the microarray housing assembly module 1. FIG. 4A is a schematic view of the second mold plate 12 of the microarray housing assembly module 1 prior to installation of the microarray M thereon, and FIG. 4B is a schematic view of the second mold plate 12 of the microarray housing assembly module 1 installed with the microarray thereon. In the embodiment, the pipette tip 50 is made of plastic for serving as a disposable component, and the tip-rack storing module 4 stores a plurality of tip racks 40 utilized for storing the pipette tips 50. When the pipette tips 50 of the tip rack 40 are deplete, the used tip rack 40 can be automatically replaced by a new one, i.e., a new tip rack provided with new pipette tips, from the tip-rack storing module 4.

In FIG. 3, a rectangular gasket 13 is detachably disposed in a rectangular slot 1100s formed on the first conjunctive surface 110 of the first mold plate 11, thereby protruding from the first conjunctive surface 110 of the first mold plate 11 to form a predetermined region 1100. The drops of the biological sample solution s1 are applied on the predetermined region 1100 enclosed by the protruded gasket 13 disposed on the first conjunctive surface 110 of the first mold plate 11. In FIGS. 4A and 4B, a positioning seat 1200 is formed on the second conjunctive surface 120 of the second mold plate 12, and the microarray M having a reaction region m100 is disposed on the positioning seat 1200 of the second mold plate 12. When the microarray M is disposed on the positioning seat 1200 of the second mold plate 12, the reaction region m100 of the microarray M is exposed to the exterior. In the embodiment, the positioning seat 1200 is a recess formed on the second conjunctive surface 120 of the second mold plate 12. As shown in FIG. 2A, the microarray M attached with drops of the biological sample solution s1 and bubbles b1 is enclosed in the microarray housing assembly module 1 when the first and second mold plates 11 and 12 are assembled, and the reaction region m100 of the installed microarray M is substantially parallel to the conjunctive area 100c of the microarray housing assembly module 1. Thus, an accommodating room 100 is formed by the gasket 13, the first mold plate 11, the microarray disposed between the first and second mold plates 11 and 12, thereby enclosing the biological sample solution s1 and bubbles b1 therein.

Figure 5:
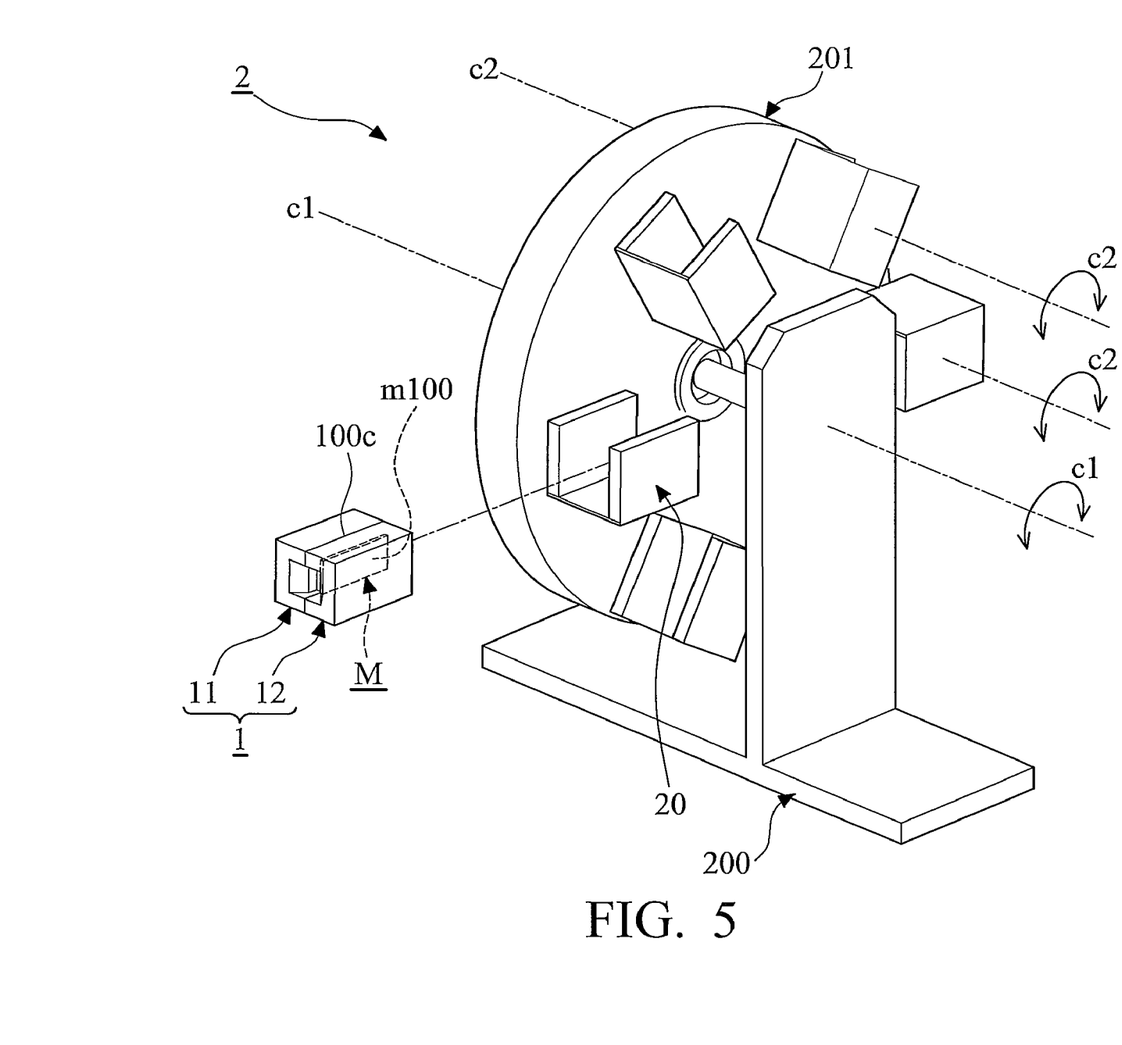
FIG. 5 is a perspective view of an incubation module of the invention.

In FIG. 5, the incubation module 2 comprises a base 200, a disk-like plate 201 rotatably disposed on the base 200, and a plurality of carrier 20 rotatably disposed on the plate 201 and circumferentially arranged. The plate 201 disposed on the base 200 is rotated about a first axis c1-c1, and each carrier 20 disposed on the plate 201 is rotated about a second axis c2-c2. The carriers 20 are utilized to fix the microarray housing assembly modules 1, respectively. The second axis c2-c2 different from the first axis c1-c1, and the first axis c1-c1 is substantially parallel to a horizontal plane. In the embodiment, the first and second axes c1-c1 and c2-c2 are substantially parallel.

When the microarray housing assembly modules 1 are respectively received in the carrier 20 of the incubation module 2, the incubation module 2 rotatably carries the microarray housing assembly module 1 with respect to the first axis c1-c1. When the incubation module 2 is rotated about the first axis c1-c1, the conjunctive area 100c of the microarray housing assembly modules 1 or the reaction region m100 of the microarray M received in the microarray housing assembly module 1 carried by the incubation module 2 is substantially perpendicular to the first axis c1-c1.

When the incubation module 2 is rotated about the first axis c1-c1, the biological sample solution s1 and the bubbles b1 are freely moved in a space formed among the reaction region m100 of the microarray M, the gasket 13 and the predetermined region 1100 enclosed by the protruded gasket 13, thereby causing the reaction region m100 of the microarray M and the biological sample solution s1 to mutually contact and to perform biochemical reaction. That is, the flow of the biological sample solution s1 received in the microarray housing assembly module 1 does not depend on an external power device or system, e.g. pump.

The tip-rack storing module 4 is utilized to automatically supply the pipette tip 50, and the temperature control module 3 is utilized to thermally modulate the biological sample solution s1 received in the pipette tip 50. The biological sample solution s1 can be heated by the temperature control module 3 from room temperature to 100° C., and the biological sample solution s1 can be cooled by the temperature control module 3 from room temperature to 0° C. That is, the temperature range of the biological sample solution s1 modulated by the temperature control module 3 is 1° C.~100° C.

In an embodiment, the biological sample feeding module 5 is an individual module detachably disposed on the first automated transport module G1, thereby supplying the power for receiving the biological sample solution s1 and applying the biological sample solution s1 on the reaction region m100 of the microarray M via the pipette tip 50. Due to the biological sample feeding module 5 being not directly contacted by the biological sample solution s1, cross contamination between the samples can be prevented.

The washing module 6 comprises three tanks 61, 62 and 63 containing different cleaning fluids (not shown in Figs.) therein, respectively. The cleaning fluids of the tanks 61, 62 and 63 are utilized to sequentially remove the biological sample solution s1 remaining on the microarray M. A circulation device (not shown in Figs.) can be further provided for respectively connecting to the tanks 61, 62 and 63 to circulate the cleaning fluids of the tanks 61, 62 and 63 in the cleaning process.

When the microarray M is removed from the tank 63 of the washing module 6 via the robot a3 of the third automated transport module G3, the microarray M is automatically moved to the drying module 7 by the third automated transport module G3 for drying. In the embodiment, the drying module 7 can be a centrifugal device or a wind blower.

Based on the described features of the automated microarray processing system E, it is noted that the automated transport modules G1, G2 and G3 mechanically hold the microarray housing assembly module 1 received with the microarray M, the biological sample solution s1 and the bubble b1 to access to the incubation module 2. The automated transport modules G1, G2 and G3 also mechanically remove the microarray housing assembly module 1 from the incubation module 2 to access the reacted microarray M from the microarray housing assembly module 1 to the tanks 61, 62 and 63 of the washing module 6. The removal of the microarray M from the microarray housing assembly module 1 is completed in the cleaning fluid of the tanks 61 of the washing module 6, as the biological sample solution s1 located on the immersed microarray M is washed by the cleaning fluids of the tanks 61, 62 and 63 of the washing module 6.

Thus, biochemical reaction of the microarray with biological sample solution and cleaning process of the reacted microarray when the biochemical reaction of the microarray is completed can be automatically performed. Thus, costs and working hours are decreased, and hybridization signals distributed by dead zones of cleaning liquid are eliminated.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. An automated microarray processing system for automatically performing biochemical reaction of a reaction region of a microarray and a biological sample solution disposed therebetween and cleaning the reacted microarray by at least one cleaning fluid when the biochemical reaction of the microarray is completed, comprising:

a microarray housing assembly module, comprising an accommodating room utilized to receive the biological sample solution with bubbles therein;

an incubation module, utilized to rotatably carry the microarray housing assembly module;

a washing module, comprising at least one tank containing the cleaning fluid; and at least one automated transport module comprising a robot with at least two degrees of freedom, wherein the robot mechanically holds the microarray housing assembly module received with the microarray, the biological sample solution and the bubbles to access to the incubation module and mechanically removes the microarray housing assembly module from the incubation module to access the reacted microarray from the microarray housing assembly module to the tank of the washing module, wherein the biological sample solution located on the immersed microarray is washed by the cleaning fluid of the tank of the washing module, wherein the microarray housing assembly module further comprises a first mold plate utilized to receive the biological sample solution, a second mold plate utilized to position the microarray, and a gasket disposed between the first and second mold plates, wherein the accommodating room is formed by the gasket, the first mold plate, the microarray disposed between the first and second mold plates.

2. The automated microarray processing system as claimed in claim 1, wherein the incubation module comprises at least one carrier utilized to fix the microarray and rotated about at least one axis, and a reaction region of the microarray received in the incubation module is substantially perpendicular to the axis.

3. The automated microarray processing system as claimed in claim 2, wherein the axis is substantially parallel to a horizontal plane.

4. The automated microarray processing system as claimed in claim 1 further comprising a temperature control module to thermally modulate the biological sample solution, wherein the temperature range of the biological sample solution modulated by the temperature control module is 0° C.~100° C.

5. The automated microarray processing system as claimed in claim 1 further comprising a biological sample feeding module utilized to supply the power to receive or apply the biological sample solution, and the biological sample feeding module further comprises a pipette tip utilized to receive the biological sample solution for applying the biological sample solution on the reaction region of the microarray.

6. The automated microarray processing system as claimed in claim 5 further comprising a tip-rack storing module utilized to automatically supply the pipette tip.

7. The automated microarray processing system as claimed in claim 1 further comprising a thermal-controlling device utilized to modulate the inner temperature of the microarray housing assembly module.

8. The automated microarray processing system as claimed in claim 1 further comprising a drying module utilized to dry the microarray moistened by the cleaning fluid when the microarray is removed from the cleaning fluid of the tank of the washing module.

9. An apparatus for automatically performing biochemical reaction of a reaction region of a microarray and a biological sample solution disposed therebetween, comprising:
a microarray housing assembly module, comprising an accommodating room utilized to receive the biological sample solution with bubbles therein;
an incubation module utilized to rotatably carry the microarray housing assembly module; and
at least one automated transport module comprising a robot with at least two degrees of freedom, wherein the robot mechanically holds the microarray housing assembly module received with the microarray, the biological sample solution and the bubbles for accessing the microarray housing assembly module to the incubation module, wherein the microarray housing assembly module further comprises a first mold plate utilized to receive the biological sample solution, a second mold plate utilized to position the microarray, and a gasket disposed between the first and second mold plates, wherein the accommodating room is formed by the gasket, the first mold plate, and the microarray disposed between the first and second mold plates.

10. The apparatus as claimed in claim 9, wherein the incubation module comprises at least one carrier utilized to fix the microarray and rotated about at least one axis, and a reaction region of the microarray received in the incubation module is substantially perpendicular to the axis.

11. The apparatus as claimed in claim 10, wherein the axis is substantially parallel to a horizontal plane.

12. The apparatus as claimed in claim 9 further comprising a temperature control module to thermally modulate the biological sample solution, wherein the temperature range of the biological sample solution modulated by the temperature control module is 0° C.~100° C.

13. The apparatus as claimed in claim 9 further comprising a biological sample feeding module utilized to supply the power to receive or apply the biological sample solution, and the biological sample feeding module further comprises a pipette tip utilized to receive the biological sample solution for applying the biological sample solution on the reaction region of the microarray.

14. The apparatus as claimed in claim 13 further comprising a tip-rack storing module utilized to automatically supply the pipette tip.

15. The apparatus as claimed in claim 9 further comprising a thermal-controlling device utilized to modulate the inner temperature of the microarray housing assembly module.

16. An apparatus for automatically cleaning a microarray attached with a biological sample solution disposed thereon by at least one cleaning fluids, comprising:
a microarray housing assembly module, comprising an accommodating room utilized to receive the biological sample solution with bubbles therein;
an incubation module utilized to rotatably carry the microarray housing assembly module;
a washing module, comprising at least one tank containing the cleaning fluid; and
at least one automated transport module comprising a robot with at least two degrees of freedom, wherein the robot mechanically removes the microarray housing assembly module from the incubation module and accessing the reacted microarray to the tank of the washing module, wherein the biological sample solution located on the immersed microarray is washed by the cleaning fluid of the tank of the washing module, wherein the incubation module comprises at least one carrier utilized to fix the microarray and rotated about at least one axis, a reaction region of the microarray received in the incubation module is substantially perpendicular to the axis, and the axis is substantially parallel to a horizontal plane and the microarray housing assembly module further comprises a first mold plate utilized to receive the biological sample solution, a second mold plate utilized to position the microarray, and a gasket disposed between the first and second mold plates, wherein the accommodating room is formed by the gasket, the first mold plate, the microarray disposed between the first and second mold plates.

17. The apparatus as claimed in claim 16 further comprising a temperature control module to thermally modulate the biological sample solution, wherein the temperature range of the biological sample solution modulated by the temperature control module is 0° C.~100° C.

18. The apparatus as claimed in claim 16 further comprising a thermal-controlling device utilized to modulate the inner temperature of the microarray housing assembly module.

19. The apparatus as claimed in claim 16 further comprising a drying module utilized to dry the microarray moistened by the cleaning fluid when the microarray is removed from the cleaning fluid of the tank of the washing module.

* * * * *